United States Patent [19]
Gergely et al.

[11] Patent Number: 5,312,626
[45] Date of Patent: May 17, 1994

[54] LOZENGE OR CHEWABLE TABLET

[76] Inventors: Gerhard Gergely; Thomas Gergely; Irmgard Gergely, all of Gartengasse 8, A-1053 Vienna, Austria

[21] Appl. No.: 907,507

[22] Filed: Jul. 1, 1992

[30] Foreign Application Priority Data

Jul. 1, 1991 [CH] Switzerland .......... 1943/91

[51] Int. Cl.$^5$ .................................. A61K 9/28
[52] U.S. Cl. ........................ 424/441; 424/44; 424/48; 424/466; 424/481; 424/686
[58] Field of Search ............ 424/441, 466, 44, 48, 424/686, 481

[56] References Cited

U.S. PATENT DOCUMENTS

| | | | |
|---|---|---|---|
| 4,650,669 | 3/1987 | Alexander | 424/700 |
| 4,664,915 | 5/1987 | Simonian | 424/44 |
| 4,762,702 | 8/1988 | Gergely | 424/44 |
| 4,867,942 | 9/1989 | Gergely | 424/489 |
| 4,867,989 | 9/1989 | Silva | 424/441 |
| 5,037,657 | 8/1991 | Jones | 424/466 |
| 5,096,714 | 3/1992 | Kuhrts | 424/439 |

Primary Examiner—Gabrielle Phelan
Attorney, Agent, or Firm—Ostrolenk, Faber, Gerb & Soffen

[57] ABSTRACT

The lozenge or chewable tablet contains, as the base, at least 30, preferably 50 to 70, percent by weight of an alkali metal and/or alkaline earth metal salt of at least one edible, organic acid, at least 10, preferably 20 to 40, percent by weight of a mixture of at least one unreacted, edible organic acid with at least one unreacted alkali metal or alkaline earth metal carbonate and/or bicarbonate and, if required, a pharmaceutical active substance and/or other conventional tablet assistants, such as flavors and sweeteners, disintegrants, hydrocolloids, etc. It contains essentially the dibasic alkali metal and/or alkaline earth metal salt of a tribasic, edible, organic acid, in particular of citric acid, and preferably an edible, organic acid, which in particular has reacted only partially to give the alkali metal and/or alkaline earth metal salt, in particular malic acid, which is stronger than the tribasic acid, and if required—based on the total tablet weight—1 to 10, preferably 3 to 7, percent by weight of at least one disintegrant, in particular about 3 percent by weight each of starch and cross-linked polyvinylpyrrolidone.

15 Claims, No Drawings

LOZENGE OR CHEWABLE TABLET

Known lozenges or chewable tablets, in particular those containing pharmaceutical active substances, generally have an insipid taste; in particular tablets which contain calcium carbonate or magnesium salts as the active substance have a chalky or an unpleasant aftertaste. Tablets or directly consumable granules which have a slight effervescent effect as a result of the addition of small amounts of effervescent mixture, for example consisting of an edible organic acid and an alkali metal and/or alkaline earth metal carbonate and/or bicarbonate, have therefore already been proposed. If a larger amount of effervescent components, such as acid and bicarbonates, are added, the pronounced effervescent effect is found by many people to be unpleasant or too acidic, since, during sucking or chewing, the acid first partially dissolves and only thereafter reacts with the bicarbonates or carbonates. Another disadvantage is that the residual moisture in the tablet causes an undesirable reaction of the effervescent components during storage, with the result that the shelf life is adversely affected. If only small amounts of effervescent components are added, the effervescent effect may disappear almost completely as a result of this reaction during storage.

It is therefore the object of the invention to provide a lozenge or chewable tablet, in particular for the administration of pharmaceutical active substances, as well as for the elimination of deficiency symptoms, in particular in the form of calcium or magnesium doses, which avoids the above-mentioned disadvantages, produces an entirely pleasant sensation when taken and also leaves behind a pleasant after-taste. This is achieved, according to the invention, by the realization of the measures described below More, greatly improved, embodiments of the invention are also described.

The preparation of the tablet according to the invention can be carried out similarly to the method described in DE-C2-3627475, except that citric acid and calcium carbonate are allowed to react to about two thirds and not only up to a certain time, as stated there. The remaining third of the acidic groups then reacts with excess free carbonate during chewing or sucking in the mouth, in particular with the action of moisture and of the body temperature of about 37° C., with very slight tingling; owing to the formation of a concentrated solution and because of the presence of the hydrocolloid, which has a breaking effect, there is however by no means a complete reaction, not even by the time the components have been swallowed.

In principle, it is also possible to mix calcium citrate or trimagnesium dicitrate with small amounts of carbonate and either small amounts of acid or with an acidic calcium or magnesium citrate and the remaining tablet components, and a similar although not quite so advantageous effect as in the procedure first described is also achieved therewith, because the carbonate in this case is not enclosed within the granular particles formed, as in the first case, and can therefore act intensively from the inside outward. Nevertheless, the second variant of a simple mixture may be sufficient for certain applications. However, the invention has the advantage of producing the corresponding alkali metal or alkaline earth metal salts in the course of granulation in the process step from the cheap carbonates, such as, for example calcium carbonate and/or magnesium carbonate, for this purpose; there is no need to use the dibasic salts which are difficult to obtain and furthermore expensive. The percentage of salts to be formed optimally for a particular product can be controlled through the reaction.

The tablet according to the invention has been found to be particularly expedient for the combined administration of calcium with fluorine. It is therefore possible to produce a chewable tablet containing, for example, 500 mg of calcium in combination with, for example, a sustained-release form of sodium monofluorophosphate (corresponding to 75 to 200 mg of sodium monofluorophosphate) and thus to achieve a pleasant and appropriate dosage form. The particular dose desired can be accommodated without difficulty in the form of particles having a particle size of from 0.1 to 0.5 mm in a tablet according to the invention and of suitable size, this being difficult to achieve, for example, in a drinking solution prepared from a conventional effervescent tablet, since the sustained-release particles of the active substance are difficult to bring into suspension or to keep in suspension.

The combination of acetylsalicylic acid and magnesium, which is particularly desirable for certain therapies, can also be particularly expediently accommodated in the dosage form according to the invention.

EXAMPLE 1

1250 parts by weight of finely powdered calcium carbonate are placed in a vacuum vessel whose jacket temperature is 90° C., and 125 parts by weight of water are then sucked in and are distributed in the course of 5 minutes while mixing. Thereafter, 970 parts by weight of powdered citric acid and 330 parts by weight of malic acid are added. The vessel is evacuated to 700 mbar and the reaction is allowed to continue until the vacuum reaches a value of 950 mbar. This defined reaction takes place in the course of 10 minutes, when the mass has reached a temperature of 60° C. In a further step, 60 parts by weight of water are sucked in and are allowed to react for 5 minutes; the process is then repeated with 50 parts by weight in the course of 15 minutes. Thereafter, 50 parts by weight of a guar gum are added and the defined reaction is allowed to continue for 15 minutes while stirring. The product is finally dried by means of a vacuum with slow stirring and is discharged via a sieve. Tablets of 3.36 g each are obtained by compressing the resulting granules with the addition of carbohydrates, disintegrants and sweeteners and flavors; for example, the following amounts of additives may be used (amounts in mg):

2500 of granules
200 of mannitol
300 of fructose
100 of polyvinylpyrrolidone (Polyplasdone XL (R)
20 100 of rice starch
and sweeteners and flavors.

EXAMPLE 2

A sustained-release sodium monofluorophosphate (corresponding to 50 to 200 mg of sodium monofluorophosphate) may also be added to the granules prepared as in Example 1 and converted into tablets by compressing with the corresponding additives, such as sweeteners, fillers and flavors.

EXAMPLE 3

In an analogous manner to Example 1, 1388 parts by weight of basic magnesium carbonate are introduced into the vacuum mixer, 400 parts by weight of water are then sucked in and distribution is effected in the course of 10 minutes with vibratory mixing. A total amount of 1930 parts by weight of powdered citric acid is added in four equal portions. After the introduction of each portion, the reaction is controlled in a defined manner at between 700 and 950 mbar for 15 to 20 minutes with vibratory mixing; the temperature of the contents varies between 75 and 86° C. Before the addition of the third and/or fourth batch, the vessel is expediently evacuated for a few minutes to 100 to 300 mbar and drying is thus effected. 100 parts by weight of potassium carbonate are then introduced in the same manner and are distributed. Finally, the granules are dried and are discharged through a sieve having a mesh size of 2 mm.

The progress of the reaction of the granules with the citric acid is determined by the particular pressure drop, which incidentally is a measure of the evolution of $CO_2$. Magnesium carbonate reacts more sluggishly than the calcium carbonate of Example 1; it is also softer and does not have the unpleasant sensation of a chalky consistency in the mouth. Moreover, it binds up to 7 or even 10 molecules of water per molecule and therefore requires from the outset a larger amount of water than the calcium carbonate.

3026 parts by weight of the base granules thus prepared are mixed with the following ingredients:
300 parts by weight of fructose
150 parts by weight of guar gum
400 parts by weight of mannitol
and sweetners and flavors
and the mixture is compressed to give tablets of 4 g each.

Such tablets are found to be a particularly pleasant magnesium therapy.

EXAMPLE 4

The granules according to Examples 1 and 3 can also be used to prepare a multivitamin/mineral chewable tablet by mixing
500 mg of the base granules (corresponding to 100 mg of calcium) as mentioned in Example 1 and
290 mg of the base granules (corresponding to 35 mg of magnesium) as mentioned in Example 3 with
160 mg of polyvinylpyrrolidone,
500 mg of glucose,
300 mg of sorbitol and
20 mg of guar gum,
and admixing of the vitamin mix consisting of vitamin A palmitate, thiamine mononitrate, riboflavine phosphate sodium, pyridoxine hydrochloride, cyanocobalamine, calcium pantothenate, nicotinamide, folic acid, biotin, vitamin D3 and vitamin C and tocopheryl acetate, as well as sweeteners and flavors. The vitamin dose may be 10 to 50% of the RDA value. The mixture is then compressed to give a tablet having a weight of 1.9 to 2 g.

EXAMPLE 5

The magnesium base granules described in Example 3 are also particularly suitable for producing a chewable aspirin tablet.

The following amounts can particularly expediently be mixed with an amount of base granules which corresponds to 7.5 mmol of magnesium:
300 parts by weight of apirin,
900 parts by weight of xylitol,
300 parts by weight of mannitol,
100 parts by weight of hydrocolloids,
50 parts by weight of sodium carbonate
and the desired amount of sweeteners and flavors and also the corresponding amount of lubricants and tabletting assistants.

Chewable aspirin tablets can be adjusted to the desired pH range by adding sodium carbonate; they are then particularly pleasant to take, the aspirin simultaneously being buffered by the alkali metal salts and the sodium carbonate during sucking or chewing.

We claim:

1. A lozenge or chewable tablet, which contains, as the base, at least 30 percent by weight of the reaction product of metal or alkaline earth metal salt and at least one edible, organic acid; at least 10 percent by weight of a mixture of at least one unreacted, edible organic acid with at least one unreacted alkali metal or alkaline earth metal carbonate or bicarbonate and, optionally, a pharmaceutical active substance or tablet assistants.

2. A tablet as claimed in claim 1, in which the alkali metal or alkaline earth metal salt is a dibasic of a tribasic, edible, organic acid.

3. A tablet as claimed in claim 1 which contains —based on the total tablet weight—1 to 5 percent by weight of at least one hydrocolloid.

4. A tablet as claimed in claim 7 which contains—based on the total tablet weight—1 to 10% percent by weight of at least one disintegrant.

5. A tablet as claimed in claim 1, which contains—based on the total tablet weight—20 to 40 percent by weight of calcium carbonate or magnesium carbonate, 20 to 40 percent by weight of at least one edible, organic acid and 20 to 60 percent by weight of conventional tablet assistants.

6. A tablet as claimed in claim 1, which contains—based on one millimole of magnesium —10 to 80 —mg of acetylsalicylic acid.

7. A tablet as claimed in claim 1 which contains 50 to 70% by weight of said alkali metal or alkaline earth metal salt and 20 to 40% by weight of said mixture.

8. A tablet as claimed in claim 2 in which the organic acid is citric acid.

9. A tablet as claimed in claim 3 which contains 2 to 4% by weight of guar gum.

10. A tablet as claimed in claim 4 which contains 3 to 7% of disintegrant.

11. A tablet as claimed in claim 10 in which the disintegrant is about 3% by weight of each of starch and of crosslinked polyvinylpyrrolidone.

12. A tablet as claimed in claim 5 which contains 30 to 35% by weight of calcium carbonate or magnesium carbonate, 30 to 35% by weight of at least one edible, organic acid and 30 to 50% by weight of conventional tablet assistants.

13. A tablet as claimed in claim 6 containing 30 to 50 mg of acetylsalicylic acid.

14. A tablet as claimed in claim 2 which contains an edible organic acid which is stronger than the tribasic, edible, organic acid of the alkali metal or alkaline earth metal salt.

15. In a method of administering a pharmaceutically active substance by providing the same in a lozenge or chewable tablet, the improvement which comprises employing the lozenge or chewable tablet of claim 1.

* * * * *